United States Patent [19]

Friedman et al.

[11] Patent Number: 4,707,542
[45] Date of Patent: Nov. 17, 1987

[54] IMMUNOGENIC HBSAG DERIVED FROM TRANSFORMED YEAST

[75] Inventors: Arthur Friedman, Churchville; E. Dale Lehman, Lansdale; William J. McAleer, Ambler; Ted F. Schaefer, Collegeville; Edward M. Scolnick, Wynnewood; D. Eugene Wampler, Harleysville, all of Pa.

[73] Assignee: Merck & Co., Inc., Rahway, N.J.

[21] Appl. No.: 636,514

[22] Filed: Aug. 1, 1984

Related U.S. Application Data

[63] Continuation-in-part of Ser. No. 525,345, Aug. 22, 1983.

[51] Int. Cl.$^4$ ............... A61K 39/29; C08B 37/12; C12N 15/00; C07K 3/20
[52] U.S. Cl. ............... 530/371; 530/395; 530/417; 530/415; 530/806; 530/826; 424/89; 436/820; 210/635; 210/502.1; 210/198.2; 435/5; 435/68; 435/70; 435/172.3; 435/235; 435/239; 435/255; 435/803
[58] Field of Search ............... 210/634, 635, 645, 656, 210/660-663, 666, 198.2, 502.1; 536/1.1, 3, 30, 56, 102, 112; 530/412, 415, 826, 824, 413, 810-812, 813-816, 417, 371; 435/5, 233-239, 68, 70, 172.3, 255, 803; 422/59; 436/820, 541; 424/89; 564/463

[56] References Cited

U.S. PATENT DOCUMENTS

| | | | |
|---|---|---|---|
| 3,917,527 | 11/1975 | Shaltiel | 210/635 |
| 4,145,406 | 3/1979 | Schick | 424/1.1 |
| 4,330,440 | 5/1982 | Ayers | 525/54.31 |
| 4,434,093 | 2/1984 | Zolton | 530/387 |

OTHER PUBLICATIONS

Jennissen, H. P., Collog.-Inst. Natl. Sante Recher. Med. 86:253-264 (1979) cited in Chem. Abstract CA92(13):106622u.
Vukovich, T. et al, Folia Haematol. (Leipzig) 107(1):148-151 (1980) cited in Chem. Abstract CA93(5):40663v.
Andersson, L. O. et al, Canadian Pat. No. 1076956, May 6, 1980, cited in Chem. Abstract CA93(22):210240z.
Einarsson, M. et al, J. Virol. Methods 3(4):213-228 (1981), cited in Chem. Abstract CA96(12):91530u.
Austen, D. E. et al, Thromb. Haemostas. 48(1):46-48 (1982) cited in Chem. Abstract CA97(20):168767g.
Dubois, M. F. et al, Ann. Virol. 134E(1):87-96 (1983) cited in Chem. Abstract CA98(25):213811a.
Einarsson, M. et al, J. Virol. Methods 8(3):233-241 (5-1984) cited in Chem. Abstract CA101(15):128495m.
Mishiro, S. et al. J. of Immunology 124:1589-1593 (1980).
Valenzuela, P. et al, Nature 298:347-350 (1982).
Hitzeman, R. A. et al, Nucleic Acids Research 11:2745-2763 (1983).
Miyanohara, A. et al, Proc. Natl. Acad. Sci. USA 80:1-5 (1983).

Primary Examiner—Margaret Moskowitz
Attorney, Agent, or Firm—Donald J. Perrella; Hesna J. Pfeiffer

[57] ABSTRACT

The surface antigen protein of human Hepatitis B virus is synthesized in *Saccharomyces cerevisiae* as a 23,000-26,000 dalton polypeptide, essentially free of intermolecular disulfide bonds. This antigen is a poor immunogen in animals and man. No prior precedent or method exists for efficiently converting the non-disulfide bonded antigen to a fully intermolecular disulfide bonded particle. We describe the first example of such a conversion in vitro and show that the act of this conversion enhances the immunogenicity of the antigen about 10-fold. The in vitro conversion makes practical the production of hepatitis B surface antigen from microorganisms using recombinant DNA methods.

2 Claims, No Drawings

IMMUNOGENIC HBSAG DERIVED FROM TRANSFORMED YEAST

RELATED APPLICATION

The present application is a continuation in part of our copending application Ser. No. 525,345 filed 22 Aug. 1983.

BACKGROUND OF THE INVENTION

Currently a vaccine is available which can be used to immunize susceptible persons against infection by hepatitis B virus. This vaccine is derived by purification of the spherical 22 nm hepatitis B surface antigen (HBsAg) from the plasma of humans who have been infected by hepatitis B virus and who have become chronic producers of surface antigen.

The human plasma-derived HBsAg is recoverable as a 22 nm particle containing both a glycosylated polypeptide (reported as having a molecular weight of 27,000–28,000 daltons) and a nonglycosylated polypeptide (reported as having a molecular weight of 23,000–26,000 daltons). This polypeptide is coded for by the HBsAg gene. Human plasma-derived HBsAg contains cholesterol and is free of phosphatidylinositol. It is stable at pH 2 and in the presence of pepsin at pH 2. It is stable also when treated with HCHO, and then with dithiothreitol and sodium dodecyl sulfate (SDS), followed by boiling for 15 minutes. After such treatment plasma-derived antigen does not migrate into an SDS-PAGE (sodium dodecyl sulfate polyacrylamide gel electrophoresis) gel. Covalent disulfide bonds exist between essentially all monomeric protein molecules of human plasma derived HBsAg. The immunogenicity of human HBsAg and thus the ability of the human HBsAg to be used as a vaccine is known to be critically dependent on the disulfide bonded form of the antigen (Mishiro et al., *J. Immunol.*, 124: 1589, 1980). If few disulfide bonds of HBsAg are present then the immunogenicity of the HBsAg is drastically reduced.

In order to insure the safety of the vaccine derived from human plasma, multiple steps are required in the purification process in order to inactivate potential contaminating infectious agents. Although this human derived vaccine has been useful, investigators have sought an alternate source for immunogenic 22 nm particles. The major approach to an alternate source has been synthesis of HBsAg in *E. coli, Saccharomyces cerevisiae* or mammalian cells using molecular cloning techniques. The gene for HBsAg has been cloned and sequenced. However, limited success has been achieved in expression of the cloned gene. The 22 nm HBsAg apparently is difficult to make in a prokaryotic organism. The synthesis of HBsAg in *Saccharomyces cerevisiae* has been reported by Valenzuela et al., *Nature*, 298, 347–350 (1982), by Hitzeman et al., *Nucleic Acid Research*, 11, 2745–2763 (1983) and by Miyanohara et al., *PNAS* 80, 1-5 (1983).

Hitzeman et al., supra, disclosed that 2–5% of the HBsAg polypeptide obtained upon yeast cell disruption is found in aggregated form similar in size, density and shape to the 22 nm particle isolated from the plasma of human hepatitis carriers. However, the nature of the interaction between the monomeric subunits in this 22 nm particle has not been investigated.

OBJECTS OF THE INVENTION

It is an object of the present invention to produce an immunogenic form of HBsAg from yeast. Another object is to provide means for converting the poorly immunogenic yeast produced HBsAg to a highly immunogenic form of HBsAg. A further object is to provide means for introducing intermolecular disulfide bonds into the poorly immunogenic HBsAg produced by yeast. Still another object is to provide a yeast produced HBsAg wherein over 90% of the HBsAg contains disulfide bonds. Yet another object is to provide a novel hydrophobic substrate for purifying HBsAg by hydrophobic interaction chromatography. These and other objects of the present invention will be apparent from the following description.

SUMMARY OF THE INVENTION

HBsAg synthesized by *Saccharomyces cerevisiae* is extracted from disrupted yeast cells. The extracted antigen, a poorly immunogenic 23,000–26,000 dalton polypeptide, is found in a form containing essentially no intermolecular disulfide bonds (Form I). The Form I antigen is converted in vitro to Form II, a dimer having intermolecular bonds between two Form I molecules. Both Form I and Form II are converted in vitro to Form III, a substantially fully disulfide bonded HBsAg particle, by various chemical treatments. Form I does not have the physical, chemical or immunologic properties of the natural antigen and can be converted in vitro to Forms II or III which possess adequate immunogenicity for formulation into a vaccine.

DETAILED DESCRIPTION

The present invention relates to immunogenic, disulfide bonded polypeptides produced by in vitro modification of HBsAg produced by transformed yeast. Over 90% of the HBsAg synthesized by transformed yeast is a poorly immunogenic non-covalently bonded, partially aggregated non-glycosylated single polypeptide of HBsAg monomers of 23,000–26,000 daltons. That the monomers are not covalently attached is shown by their migration as 23,000–26,000 dalton polypeptides under denaturing, non-reducing conditions in polyacrylamide gels containing 0.1% SDS. All of this polypeptide is present in aggregated form. This form of the HBsAg is referred to herein as Form I. The Form I polypeptide is identified as HBsAg by reaction with specific anti-Form I antibodies raised in rabbits or guinea pigs. Antigenic potency studies in mice have shown that the majority of the antigen in crude yeast extracts is insufficiently antigenic to make a practical vaccine.

Form I can be converted in vitro to a dimer, by treatment at a pH of about 8.5 or above. The dimer, referred to herein as Form II, has a particle size of from about 16 to about 25 nm, typically from about 18 to about 20 nm as visualized by electron microscopy, an aggregate size of $2-4 \times 10^6$ daltons as determined by gel filtration on Sepharose 6B, and intermolecular disulfide bonds between two HBsAg molecules. This form of the antigen migrates as a 46,000–52,000 dalton polypeptide dimer in denaturing non-reducing polyacrylamide gel electrophoresis systems. Under reducing conditions, Form II migrates as a polypeptide of 23,000–26,000 daltons. Form II is from about 5-fold to about 10-fold more immunogenic than Form I. Form II induces antibodies against plasma-derived HBsAg.

Both Form I and Form II can be subjected to various in vitro chemical treatments to yield another highly immunogenic antigen. This antigen, referred to herein as Form III, is a covalently bonded aggregate of 23,000–26,000 dalton HBsAg monomers wherein substantially all, i.e., at least about 90%, of the sulfur atoms form disulfide bonds at least part of which are intermolecular disulfide bonds. These aggregates appear as $2–4 \times 10^6$ dalton molecules by gel filtration on Sepharose 6B or 18–20 nm particles as visualized by electron microscopy. Form III fails to migrate into the separating gel under non-reducing denaturing conditions which indicates a size greater than 100,000 daltons. Under reducing conditions, Form III has a mobility equal to that of Form I indicating that Form III is a polymer of Form I stablized by interchain disulfide bonds. Form III is from about 5-fold to about 10-fold more immunogenic than Form I. Because of its high degree of intermolecular disulfide bonds, Form III is more similar to plasma-derived HBsAg than either Form I or Form II.

While comparable to plasma-derived HBsAg in particle size, density and immunological efficacy, Form III is a uniquely different molecule as shown by its differing chemical properties. Form III is irreversibly decomposed at pH 2–5. At pH 2 or 3 the decomposition is almost instantaneous; at pH 4 or 5 it takes from a few minutes to about 30 minutes at about room temperature. When treated with HCHO, and then with dithiothreitol and SDS, followed by boiling for 15 minutes, Form III, when loaded on a SDS-PAGE gel, migrates into the 25,000 dalton region of the gel. Form III is free of cholesterol and contains phosphatidylinositol.

Pyrogenic substances and protein derived from yeast cells are removed by passing the antigen across a hydrophobic substrate having substituents covalently bonded thereto by a preponderance of uncharged covalent bonds.

Form I may be converted in vitro to Form II by treatment at a pH of from about 8.5 to about 11.0 at temperatures of from about 10° C. to about 70° C. for periods of from about 10 minutes to a few hours.

Form III may be formed in vitro by treating Form I or Form II with thiocyanate or urea at a pH of from about 7.0 to about 9.5, or by treating Form I or II at an elevated pH of about 11 or above.

The thiocyanate may be an alkali metal or ammonium salt e.g., LiSCN, NaSCN, KSCN or NH$_4$SCN. The thiocyanate is employed at a concentration of about 2 M or above, preferably about 3 M, at temperatures of from about 4° C. to about 60° C. for a time period of from about 2 hours to about 15 hours. The conversion takes less time at higher temperatures.

The urea is employed at a concentration of at least about 4 M or greater, generally at a concentration of from about 4 M to about 10 M, and typically at about 8 M, at alkaline pH of from about 7.5 to about 9.5 at temperatures of from about 4° C. to about 60° C. for from about 2 hours to about 15 hours. The conversion takes less time at higher temperatures.

The elevated pH is from about 11.0 to about 12.5 at temperatures of from about 4° C. to about 60° C. for from about 2 hours to about 15 hours. The conversion takes less time at higher temperatures.

While the present invention is illustrated in the following examples with a particular transformed host, it is to be understood that the invention is not concerned with specific transformed hosts, or specific vectors, but with in vitro techniques for converting a poorly immunogenic form of HBsAg expressed by a transformed host into an immunogenic form suitable for use in a vaccine.

The following examples illustrate the present invention without, however, limiting the same thereto.

EXAMPLE 1

Preparation of Form I

A leucine deficient agar slant was inoculated with one mL of reconstituted lyophilized recombinant *Saccharomyces cerevisiae* cells, ATCC 20665, strain H52, expressing the HBsAg gene. After 4 days at 28° C. the slant was resuspended in 3 mL yeast extract-hysoy digest-dextrose (YEHD) medium and two 250 mL YEHD flasks were inoculated with 1 mL per flask. These flasks were incubated at 28° C. in a shaker/incubator at 350 rpm for 8 hours. The two flasks were pooled (O.D. of 1.2 at 660 nm and pH of 5.73) and 20 mL were used to inoculate each of two 2 L YEHD flasks. After 22 hours in an incubator/ shaker at 350 rpm and 28° C., the two 2 L flasks were pooled (total volume was 1000 mL with an O.D. of 5.0 at 660 nm and pH of 5.13).

This 1000 mL yeast culture was added to a 16 L New Brunswick fermenter (16BYF52-4) containing 6.5 L of YEHD medium. The fermentation was continued at 28° C., stirred at 500 rpm and sparged with air at a rate of 5 L/minute. The pH was controlled at 5.0 with 2 N NaOH. YEHD medium was pumped into the fermenter at a rate of 60 mL/hour from the 14th to the 40th hour.

After 40 hours the contents of the 16 L fermenter (approximately 10 L of yeast culture with an O.D. of 35 at 660 nm and pH of 5.0) were inoculated into 100 L of YEHD medium in a 250 L New Brunswick fermenter (200YF52-6) maintained at a temperature of 28° C. The culture was stirred initially at 150 rpm and sparged with air at a rate of 60 L/minute. Throughout the fermentation dissolved oxygen concentration was controlled at 20% of saturation and the pH at 5.0. After cell growth began to increase, YEHD medium was pumped into the fermenter from the 14th to the 46th hour of fermentation at the following rates:

| HOURS | RATE (L/hour) |
| --- | --- |
| 14–20 | 2 |
| 20–25 | 3 |
| 25–29 | 3.8 |
| 29–30 | 4.8 |
| 30–46 | 3 |

Approximately 150 L of yeast culture were harvested at 48 hours; the O.D. was 31.5 at 660 nm and pH was 4.95. An aliquot of cell broth was tested for uniformity; only yeast colonies were observed. Approximately 80 L of the broth were harvested in a Sharples centrifuge with a wet cell paste of 3.1 kg.

The cell paste from the Sharples bowl was suspended in 3.1 L buffer (0.1 M sodium phosphate, pH 7.2, 0.5 M NaCl) and repelleted to remove entrained medium components. The pelleted yeast cells were resuspended again in an equal volume of the same buffer.

The washed yeast cell suspension (5.6 L) was stored at 2 to 8° C. for 3 days and then adjusted to 2 mM phenylmethylsulfonylfluoride (PMSF) by adding 56 mL of a 200 mM solution of PMSF in isopropanol. The cell suspension was then pumped through a high pressure homogenizer (Manton-Gaulin Laboratory Homogenizer) at a flow rate of 1 L/minute and operating pressure of 6000 psig to rupture the cells and release the HBsAg. The suspension was centrifuged at 36 000 xg for 30 minutes and the supernatant liquid (cell extract) decanted and divided into three aliquots. The HBsAg concentration was 0.9 mg/L by Ausria. The total protein content of the same aliquot was 1,523 mg. Two portions of one aliquot were incubated at 100° C. for 5 minutes in 0.050 mL of a buffer containing 2% sodium dodecyl sulfate (SDS), 0.125 M Tris-HCl, pH 6.8. One of the two portions contained in addition 100 mM dithiothreitol (reducing conditions), while the other portion did not contain any dithiothreitol (non-reducing conditions). Samples were electrophoresed for 2.5 hours at 65 mA/gel in 12.5% separating gels, 3% stacking gels according to Laemmli, *Nature* 227: 680, 1971.

HBsAg was identified by a protein immunoblotting technique (Burnette, *Anal. Biochem.* 112: 195–203, 1981) using rabbit antiserum obtained from rabbits treated in the following way. Human plasma HBsAg (Hilleman et al., *Am. J. Med. Sci.* 270: 401, 1975) was reduced and denatured in 2% SDS, 5% 2-mercaptoethanol, 0.125 M Tris-HCl, pH 6.8, at 100° C. for 5 minutes. Four New Zealand white rabbits were each given a primary injection (intradermally and intramuscularly) of 2 mg of protein in 2 mL of a 1:1 mixture of complete Freund's adjuvant (65/35/Bu; CFA), followed by three booster injections of 1 mg of protein in CFA at monthly intervals and finally three booster injections of 0.1 mg of protein at monthly intervals.

The molecular weight of the antigen was estimated by reference to the following set of methyl-$^{14}$C labeled molecular weight standards (New England Nuclear): phosphorylase B (97,400), bovine serum albumin (69,000), ovalbumin (46,000), carbonic anhydrase (30,000) and lactoglobulin A (18,367).

Electrophoresis showed antigen migrating in the 25,000 dalton region under both reducing and non-reducing conditions. This result shows that the HBsAg protein formed in the yeast exists as a non-disulfide bonded monomer. This form of the antigen is referred to as Form I.

EXAMPLE 2

Preparation of Form II

A second aliquot of cell extract from Example 1 was mixed with fused silica (3 mg for each µg of HBsAg as measured by Ausria II) and incubated at 37–39° C. for 2.5 hours. The silica was sedimented by centrifuging (3600 rpm, 25 minutes, Beckman J-6 centrifuge, 5–10° C.), the supernatant liquid discarded, and the silica washed with PBS (phosphate buffered saline, 0.01 M sodium phosphate, pH 7.2, 0.15 M NaCl). Hepatitis B surface antigen was eluted from the silica with 5 mM sodium borate, pH 8.9–9.2 and the eluate subjected to electrophoretic analysis as described in Example 1. The results showed that under non-reducing conditions part of the antigen migrated as Form I and part migrated in the 50,000 dalton region. This 50,000 dalton protein, referred to as Form II, is a dimer of Form I since all of Form II was converted to the 25,000 molecular weight monomer (Form I) under the reducing conditions of Example 1.

EXAMPLE 3

Preparation of Form III with Thiocyanate

The third aliquot of cell extract from Example 1 was dialyzed overnight vs. 3 M ammonium thiocyanate in 0.5 M sodium chloride, and 0.1 M sodium phosphate, pH 7.2. A protein precipitate was removed by centrifugation and the supernatant liquid dialyzed extensively vs. PBS to remove ammonium thiocyanate. The thiocyanate treated product was subjected to electrophoretic analysis as described in Example 1. The results showed a form of the antigen which was too large to enter the running gel in the non-reducing conditions. This form of the antigen has a particle weight greater than 100,000 daltons and is referred to as Form III. Form III is a disulfide bonded particle since it is converted to the 25,000 molecular weight monomer of Form I under the reducing conditions of Example 1.

EXAMPLE 4

Preparation of Form III with Urea

A sample of the supernatant liquid prepared as described in Example 1 was treated with fused silica as described in Example 2 and then passed over a column of ECTHAM-cellulose. The effluent was dialyzed against a solution of 8 M urea in 0.01 M Tris-HCl, pH 8.1 for 16 hours. The urea was then removed by dialysis against three changes of PBS. The final dialyzed sample was analyzed by gel electrophoresis as described in Example 1. The results showed quantitative conversion of the antigen to Form III.

EXAMPLE 5

Preparation of Form III by High pH after ECTHAM-Cellulose Purification

A sample of the supernatant liquid, prepared as described in Example 1, was treated with fused silica as described in Example 2 and then passed over a column of ECTHAM-cellulose. Portions of the purified HBsAg effluent (protein=90 µg/mL, HBsAg=66 µg/mL) were mixed with an equal volume of either 6.25 mM sodium phosphate buffer (pH 7.2) containing 0.15 M NaCl; 0.2 M Tris-HCl (pH 7.5), 0.05 M sodium borate (pH 8.5, 9.5, 10.5); or 0.1 M Na$_2$HPO$_4$, pH 11.5, or 0.1 M KCl, NaOH, pH 12.5 and incubated at 37° C. for 4 hours. The mixtures were dialyzed 16 hours vs. PBS at 4° C. and analyzed by electrophoresis as described in Example 1.

Electrophoresis under denaturing non-reducing conditions showed that samples incubated at pH 11.5 or 12.5 were quantitatively converted from Forms I and II to Form III. None of the other pH treatments caused a significant amount of conversion.

EXAMPLE 6

Preparation of Form III by High pH After Fused Silica Treatment

A portion of the product of Example 2, 0.5 mL, (protein=3700 µg/mL, HBsAg=1100 µg/mL) was mixed with an equal volume of 6.25 mM sodium phosphate buffer (pH 7.2) containing 0.15 M NaCl, 0.2 M Tris-HCl (pH 7.5), 0.05 M sodium borate (pH 8.5, 9.5, 10.5), or 0.1 M Na$_2$HPO$_4$, pH 11.5 and incubated at 37° C. for 4 hours. The mixture was dialyzed 16 hours vs. PBS at 4° C. and analyzed for HBsAg by Ausria and electrophoresis.

Electrophoresis under denaturing non-reducing conditions showed that HBsAg incubated at pH 11.5 was quantitatively converted from Forms I and II to Form III. Conversely, none of the other pH treatments caused a significant amount of conversion.

EXAMPLE 7

Relative Potency of Form III/Form I

To assess in vivo potency, portions of three aliquots from Examples 1-3 were diluted to contain 0.1 μg/mL of HBsAg as measured by the subunit assay (see footnote to Table 1) and adsorbed onto alum by adding 0.085 mL of a sterile 10% solution of potassium aluminum sulfate, with stirring, to each mL of sample and the pH of the mixture raised to 6.75 with 1 N NaOH. After stirring for two hours, the suspension was centrifuged 10 minutes at 1800 xg and the supernatant liquid decanted from the alum precipitate. The alum-adsorbed HBsAg was resuspended in physiological saline to the original volume and thimerosal was added to a concentration of 1:20,000. The preparation was tested in mice undiluted and diluted in alum placebo to contain 0.025, 0.006 and 0.0016 μg/mL. One milliliter of each preparation, or alum placebo, was injected intraperitoneally into each of 10 mice. The mice were individually bled 28 days later and antibody titers were measured by the Ausab radioimmune assay (Abbott). Data were analyzed to determine seroconversion rates to the different doses of subunit HBsAg. A probit analysis was performed, plots of empirical probit versus dose were made, iterative maximum likelihood least squares performed on the data and $ED_{50}$ values (μg) were obtained.

The results are presented in Table 1.

TABLE 1

Immunological Analysis of Unpurified Yeast-Derived Hepatitis B Virus Surface Antigen

|  | In Vitro Subunit HBsAg[1] (μg/ml) | In Vivo $ED_{50}$ (μg)[2,3] | HBsAg/$ED_{50}$ |
|---|---|---|---|
| Form I | 0.10 | 0.12 | 0.83 |
| Form III | 0.10 | 0.012 | 8.33 |
| Forms I & II (from Example 2) | 0.10 | 0.011 | 9.1 |

[1]Subunit HBsAg Assay
Samples for analysis were reduced and denatured by incubation for 5 minutes at 100° C. in 2% SDS, 50 mM dithiothreitol, 0.5 M Tris-HCl, pH 8.0. The samples were cooled to 4° C., flushed with $N_2$ for 30 seconds and alkylated in 100 mM iodoacetamide, 0.5 M Tris-HCl, pH 8.0. Serial fivefold dilutions from 1:100 to 1:12,500 in NET buffer (0.15 M NaCl, 5 mM EDTA, 50 mM Tris-HCl, pH 7.4, 0.02% $NaN_3$) containing 2% bovine serum albumin (BSA) were analyzed.
The radioimmune assay was performed in 20 well plastic reaction trays. Rabbit antiserum, (obtained as described on Page 10) was diluted in NET buffer containing 2% BSA and 0.1 mL was mixed with 0.3 mL of sample for analysis or standard. The mixture was incubated 2 hours at 37° C. To each well was added a 0.6 cm polystyrene bead which had been passively coated with subunit HBsAg and the mixture was incubated at 23° C. for 16 hours. The supernatant liquid was aspirated, the beads washed and $6 \times 10^4$ cpm of [$^{125}$I] Protein A (70-100 μCi/μg) in 0.2 mL of NET buffer containing 2% BSA was added to each well and allowed to incubate at 37° C. for 1 hour. The supernatant liquid was aspirated, the beads washed and the amount of Protein A bound to the beads was determined with a gamma counter. The amount of soluble subunit HBsAg was determined from the degree of inhibition of Protein A binding.
[2]Native HBsAg. The Abbott Ausria II kit was used to measure the quantity of native HBsAg.
[3]$ED_{50}$ is the amount of antigen required to seroconvert 50% of

TABLE 1-continued

Immunological Analysis of Unpurified Yeast-Derived Hepatitis B Virus Surface Antigen the animals as described in this Example.

EXAMPLE 8

Relative Potency of Crude Yeast Cell Extract

YED agar was inoculated with 1 mL of reconstituted lyophilized recombinant *Saccharomyces cerevisiae* cells, ATCC 20665, strain H52 and incubated at 28° C. for 72 hours. A single colony was used to inoculate a 250 mL YEHD flask. The flask was incubated at 28° C./350 rpm for 7.5 hours. Ten mL of this culture was used to inoculate a 2 L YEHD flask, which was then incubated at 28° C./350 rpm for 38.5 hours. The final $OD_{660}$ and pH of the culture were 10.2 and 6.06, respectively. These cells were harvested by centrifugation and broken by vigorous agitation in the presence of glass beads. The crude supernatant liquid was clarified by centrifugation (16,000 xg for 20 minutes at 4° C.), diluted to 1 mg protein per mL and adsorbed to alum.

The alum adsorbed antigen was tested for antigenicity in mice. The results showed an $ED_{50}$ of 18 μg based on the subunit RIA assay. This is some 25 to 50 times less antigenic than purified Form III and indicates that form I is not antigenic in mice.

EXAMPLE 9

Preparation of Vaccine from Immune Affinity Purified Form III

A leucine deficient agar slant was inoculated with one mL of reconstituted lyophilized recombinant *Saccharomyces cerevisiae* cells, ATCC 20665, strain H52, expressing the HBsAg gene. After 4 days at 28° C. the slant was resuspended in 3 mL YEHD medium and two 250 mL YEHD flasks were inoculated with 1 mL per flask. These flasks were incubated at 28° C. in a shaker/incubator at 350 rpm for 8 hours. The two flasks were pooled (O.D. of 1.2 at 660 nm and pH of 5.73) and used to inoculate two 2 L YEHD flasks using 20 mL per flask. After 22 hours in an incubator/shaker at 350 rpm and 28° C., the two 2 L flasks were pooled (total volume was 1000 mL with an O.D. of 5.0 at 660 nm and pH of 5.13).

This 1000 mL of yeast culture was added to a 16 L New Brunswick fermenter (16BYF52-4) containing 6.5 L of YEHD medium. The fermentation was continued at 28° C., stirred at 500 rpm and sparged with 5 L/minute of air. The pH was controlled at 5.0 with 2N NaOH. After approximately ten hours into the fermentation, additional YEHD medium was pumped into the fermenter until 40 hours.

After 40 hours the contents of the 16 L fermenter (approximately 10 L of yeast culture with an O.D. of 35 at 660 nm and pH of 5.0) were added to 100 L of YEHD medium in a 250 L New Brunswick fermenter (200YF52-6). The culture was stirred initially at 150 rpm and sparged with 60 L/minute of air. Throughout the fermentation dissolved oxygen was controlled at 20% of saturation and pH at 5.0. After cell growth began to increase, YEHD medium was pumped into the fermenter from the 14th hour of fermentation until the end of the fermentation. Approximately 150 L of yeast culture were harvested at 48 hours; the O.D. was 31.5 at 660 nm and pH was 4.95. An aliquot of cell broth was tested for uniformity; only yeast colonies were observed. Approximately 80 L of the broth were harvested in a Sharples centrifuge to give a wet cell paste.

The cell paste from the Sharples bowl was resuspended in an equal volume of buffer (0.1 M sodium phosphate, pH 7.2, 0.5 M NaCl) and repelleted to remove entrained medium components. The pelleted, washed yeast cells were resuspended in an equal volume of the same buffer.

The washed yeast cell suspension was stored at 2–8° C. for 3 days and then adjusted to 2 mM PMSF by adding 1% of a 200 mM solution of PMSF in isopropanol. The cell suspension was then pumped through a high pressure homogenizer (Manton-Gaulin Laboratory Homogenizer) at a flow rate of 1 L/minute and operating pressure of 6000 psig to rupture the cells and release the HBsAg. The suspension was passed through the homogenizer nine times to complete the cell rupturing with the suspension recooled to 0–10° C. between each pass. The ruptured cell suspension was stored at 2–8° C. for one day.

The ruptured cell suspension was diluted with an equal volume of pH 7.2 buffer and adjusted to contain 0.1% nonionic surfactant [polyoxyethylene(9) octaphenol]. The diluted suspension was passed across a 0.22 micron membrane unit operated in a tangential flow mode and diafiltered with six volumes of pH 7.2 buffer containing 0.1% polyoxyethylene(9)octaphenol to separate the antigen from the cell debris. The filtrate containing the antigen was concentrated to 6.8 L in a hollow fiber membrane (H10x100), and then treated with polystyrene-divinyl benzene beads to remove the nonionic surfactant. The solution was diafiltrated with five volumes of pH 7.2 buffer and then further concentrated on the hollow fiber membrane unit to 135 mL. The concentrate was stored at 2–8° C. for 1 day.

The concentrate was then adjusted to 0.1 mM PMSF by adding 1.3 mL of 100 mM PMSF in isopropanol and incubated with 14 g fused silica for 3 hours at 37° C. to adsorb the antigen onto the silica. The silica was recovered by centrifugation and washed twice with physiological saline solution. The washed silica was then incubated for 20 minutes at 56° C. with pH 9.1 buffer (200 mL) containing 5 mM borate and 0.25% desoxycholate to elute the antigen. After centrifugation to remove the antigen-containing supernatant liquid, the incubation was repeated to complete recovery of the antigen. The two supernatant liquids were pooled (413 mL) and stored at 2–8° C.

To a portion of the partially purified antigen was added PMSF and ethylenediamine-tetraacetic acid (EDTA) to final concentrations of 2 mM each. The solution was passed over an affinity column of goat antibody to hepatitis B surface antigen which adsorbed the hepatitis B antigen from the silica product. The flow rate through the column was 150 mL per hour. After the silica product had entered the column, it was held for ½ hour and then washed with 250 mL of pH 7.2 buffer. The antigen was eluted from the affinity column using 3M ammonium thiocyanate in pH 7.2 buffer. The antigen rich fractions were pooled and thiocyanate removed by dialysis against PBS.

To 82 mL of purified antigen was added 618 mL of PBS to give 700 mL of diluted antigen. This contained a calculated protein concentration of 11 μg/mL.

To 675 mL of the diluted antigen was added, with stirring, 6.75 mL of a 1:40 dilution in distilled water of formaldehyde. The mixture was placed in a 37° C. incubator on a magnetic base. After 24 hours, the material was transferred aseptically to a fresh sterile bottle and replaced on a magnetic base at 37° C. After 72 hours, the aqueous bulk was removed from the incubator and 1.9 mL of 1% thimerosal added. After removal of a 6 mL sample, the material was stored at 2–8° C.

To 675 mL of aqueous bulk was added 57.4 mL of 10% alum with magnetic stirring and the pH was brought to 6.7 by the addition of 15.5 mL of 1 N sodium hydroxide. After stirring 2 hours at room temperature, the alum precipitate was centrifuged 10 minutes at 3000 rpm in a Sorvall centrifuge and resuspended in saline to the original volume. Thimerosal, 3.4 mL of a 1% solution, was added to the alum adsorbed vaccine to make a final concentration of 1:20,000.

The alum adsorbed vaccine was dispensed in 1.25 mL amounts in glass vials, the vials were stoppered, sealed, labeled and stored at 4° C.

All steps of this example were carried out using sterile reagents and equipment and sterile technique.

EXAMPLE 10

Preparation of Vaccine From Biochemically Purified Form III

Antigen prepared from the extract of broken yeast cells prepared as described in Example 1 which had been adsorbed onto and eluted from fused silica as described in Example 3 was purified in the following way.

Fused silica desorbed antigen (11.9 mL, 735 mg protein) was dialyzed against 2×4 L of 50 mM (N-morpholino)propanesulfonic acid (MOPS), pH 7 (starting buffer) to equilibrate it with the buffer to be used for hydrophobic interaction chromatography on butyl agarose. A column of butyl agarose, 150 mL bed volume, was equilibrated with 50 mM MOPS, pH 7.0, and the dialyzed fused silica product was pumped onto the column at 150 mL/hour. When all the sample had entered the column it was washed with 750 mL of starting buffer to remove unbound protein. Analysis of the composition of the unbound protein effluent showed that more than 95% of the yeast pyrogenic substances were present in the effluent. The HBsAg was adsorbed onto the column and was removed by eluting the column with 750 mL of 0.1% polyoxyethylene(9)octaphenol and 50 mM MOPS, pH 7.0. Fractions containing HBsAg were detected with the Ausria II kit and were pooled.

Polyoxyethylene(9)octaphenol was removed from the antigen containing solution by treatment with polystyrene beads cross-linked with divinylbenzene (Amberlite XAD-2 resin) using 1 gm resin/35 mg polyoxyethylene(9)octaphenol. The detergent free antigen then was concentrated 5 fold in an ultrafiltration cell fitted with an XM-100 membrane (Amicon).

A 24.5 mL sample containing 19.1 mg protein was applied to a 390 mL Sepharose 6B column and the column eluted with PBS at 60 mL/hour. A pool of purified HBsAg was made from those protein containing fractions which were positive for HBsAg by Ausria II and which had typical ultraviolet spectra of HBsAg. This pool eluted just behind the void volume of the column and contained a mixture of purified Forms I and II.

Purified Form III was obtained by mixing an equal volume of 6 M KSCN in PBS with the antigen pool obtained from Sepharose 6B chromatography. The KSCN was removed by extensive dialysis against PBS.

The purified Form III, 6.22 mg in 111 mL was sterile filtered (0.22 μ pore size), diluted to 44 μg/mL by addition of 30 mL of PBS. Of the foregoing solution, 132 mL were diluted to use concentration of 10 μg/mL by adding 488 mL of PBS. The diluted product was then treated with formaldehyde and adsorbed to alum as described in Example 9.

The butyl agarose used in this example was synthesized by covalently linking n-butylamine to agarose beads via activation of the agarose with CNBr following the procedure described in *Methods in Enzymology*, Jakoby and Wilchek, editors, Vol. 34, page 130, 1974, Academic Press, New York. Activation of agarose beads with CNBr and subsequent covalent coupling of primary amine ligands is widely practiced because it is a straightforward reaction. The reaction, however, yields at least three different products: an isourea derivative, an N-substituted imidocarbamate and an N-substituted carbamate. For hydrophobic interaction chromatography procedures it is undesirable to have the first two of these products because they have a positive charge at physiologic pH values. The third linkage, the N-substituted carbamate, is uncharged and suitable for hydrophobic interaction chromatography procedures at physiologic pH values.

Fortunately, the amount of the positively charged first and second linkages can be limited by careful control of the concentration of butylamine and the pH in the reaction mixture during manufacture of butyl agarose. Furthermore the quality control of the butyl agarose includes measuring the total capacity of the wet gel by determining butylamine content by nuclear magnetic resonance spectroscopy, and by measuring the amount of positive charge by chloride ion titration.

By experience it has been determined that suitable preparations of butyl agarose are those containing 4–13 μmoles of butylamine per mL of resin and wherein less than 50% of the total number of butylamine groups are bound to the gel by positively charged bonds (chloride binding assay).

EXAMPLE 11

Purification of Recombinant HBsAg from Yeast by Hydrophobic Interaction Chromatography A sample of the supernatant liquid prepared as described in Example 1 was treated with fused silica as described in Example 2. It was the dialyzed against 10 mM Tris-HCl, pH 7.5 for 4 hours and immediately sub-divided into 1.0 mL aliquots. Each aliquot was applied separately to 1.0 mL columns of either 4% agarose, ethyl agarose, butyl agarose, phenyl Sepharose CL-6B (Pharmacia), hexyl agarose, octyl agarose or decyl agarose which were equilibrated with 10 mM Tris, pH 7.5.

After the sample aliquot had entered the columns each was washed with 5 mL of 10 mM Tris-HCl, pH 7.5 to remove unadsorbed proteins. Each column was then eluted with 50% ethylene glycol. The column charge, unadsorbed fraction and ethylene glycol eluate were analyzed for HBsAg by AUSRIA II and for purity by SDS-PAGE (silver staining).

The results were that recombinant HBsAg was not bound to agarose 4B or ethyl agarose and was recovered in the unadsorbed fraction whereas it was bound to butyl, phenyl, hexyl, octyl and decyl agarose. The antigen was eluted from butyl, hexyl, octyl and decyl agarose and phenyl Sepharose CL-4B with ethylene glycol.

Analysis by SDS-PAGE (silver staining) showed that fraction eluted from the hydrophobic interaction column by 50% ethylene glycol were highly purified (>90%) HBsAg.

EXAMPLE 12

Preparation of Vaccine from Biochemically Purified Form II

A cell extract prepared as described in Example 9 was mixed with fused silica (3 mg for each μg of HBsAg as measured by Ausria II) and incubated at 37–39° C. for 2.5 hours. The silica was sedimented by centrifuging (3600 rpm, 25 minutes, Beckman J-6 centrifuge, 5–10° C.), the supernatant liquid discarded, and the silica washed with PBS. Hepatitis B surface antigen was eluted from the silica with 0.005M borate, pH 8.9–9.2, and 0.25% desoxycholate.

The eluted antigen (16 mL, 106 mg protein) was centrifuged at 10,000 rpm for 10 minutes at 4° C. to yield 14.4 mL of supernatant liquid. A 10 mL aliquot of the supernatant liquid containing 51 mg protein was pumped onto an ECTHAM-cellulose column (2.6 cm diameter, 15.5 cm high, 82 mL bed volume) which was previously equilibrated with 5 mM NaCl, 6.25 mM Tris and 0.5 mM MgCl$_2$, pH 7.5, at 4° C. The column then was washed with 134 mL of the foregoing buffer and eluted with a 0–2 M NaCl gradient in the foregoing buffer (total volume 500 mL). The unadsorbed fraction contained 7.95 mg of purified HBsAg in 13 mg of total protein.

A 24.5 mL sample containing 19.1 mg protein was applied to a 390 mL Sepharose 6B column and the column eluted with PBS at 60 mL/hour. A pool of purified HBsAg was made from those protein containing fractions which were positive for HBsAg by Ausria II and which had typical ultraviolet spectra of HBsAg. This pool eluted just behind the void volume of the column and contained a mixture of purified Forms I and II.

Purified Form III was obtained by dialyzing 208 μg (7.7 mL) of the sepharose 6B purified antigen against 4 L of 3 M ammonium thiocyanate in PBS, pH 7.2, for 16 hours. The ammonium thicyanate was removed by extensive dialysis against PBS.

The purified Form III, 7.1 mL, was diluted to 10 μg/mL by adding 12.0 mL of PBS and adsorbed to alum as described in Example 9.

What is claimed is:

1. A method of removing pyrogenic substances and yeast protein from HBsAg produced in yeast cells which comprises passing the HBsAg across a hydrophobic substrate formed by bonding butylamine to agarose by a preponderance of N-substituted carbamate bonds, for a time and under conditions sufficient to adsorb the HBsAg to said substrate.

2. A method according to claim 1 wherein the butylamine is n-butylamine.

* * * * *